United States Patent [19]

Wolfram

[11] Patent Number: 4,647,709

[45] Date of Patent: Mar. 3, 1987

[54] PROCESS FOR RING-CHLORINATING TOLUENE

[75] Inventor: Hans Wolfram, Kelkheim, Fed. Rep. of Germany

[73] Assignee: Hoechst Aktiengesellschaft, Frankfurt am Main, Fed. Rep. of Germany

[21] Appl. No.: 770,714

[22] Filed: Aug. 29, 1985

[30] Foreign Application Priority Data

Aug. 31, 1984 [DE] Fed. Rep. of Germany ....... 3432095

[51] Int. Cl.$^4$ .............................................. C07C 17/12
[52] U.S. Cl. .................... 570/209; 570/210
[58] Field of Search .................. 570/209, 210

[56] References Cited

U.S. PATENT DOCUMENTS

| | | | |
|---|---|---|---|
| 4,069,263 | 1/1978 | Lin | 570/209 |
| 4,190,609 | 2/1980 | Lin | 570/209 |
| 4,289,916 | 9/1981 | Nakayama et al. | 570/209 |

FOREIGN PATENT DOCUMENTS 0063384 10/1982 European Pat. Off.
56-110630 9/1981 Japan.

OTHER PUBLICATIONS

Organic Syntheses, Coll. vol. 2, pp. 485–486.

Primary Examiner—Natalie Trousof
Assistant Examiner—Joseph A. Boska
Attorney, Agent, or Firm—Curtis, Morris & Safford

[57] ABSTRACT

In the ring chlorination of toluene, a particularly high proportion of p-chlorotoluene is obtained by using in addition to the customary Lewis acid catalysts as cocatalyst a chlorination product of 2,8-dimethylphenoxathiin which comprises in the main 1,3,7,9-tetrachloro-2,8-dimethylphenoxathiin of the formula

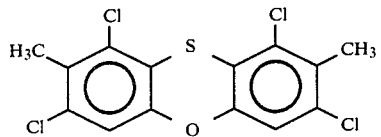

9 Claims, No Drawings

PROCESS FOR RING-CHLORINATING TOLUENE

Toluene is ring-chlorinated using the methods customary for the ring halogenation of aromatic compounds. The products formed in the monochlorination of toluene are primarily o- and p-chlorotoluene besides a minor amount of the m-isomer and, in certain circumstances, also of products with a higher degree of chlorination and chlorination in the methyl group. Of the ring-chlorinated monochlorotoluenes it is in particular the p-isomer which is economically important as an intermediate for a large number of organic syntheses. There has therefore been no shortage of attempts to steer the ring chlorination of toluene toward an increase in the proportion of p-chlorotoluene.

For instance, according to the process for ring-chlorinating toluene described in Japanese Offenlegungsschrift No. 56(=1981)-110,630 of the firm of Hodogaya Kagaku Kogyo K.K., increased formation of the p-Cl isomer can be obtained by using in addition to the customary Lewis acid catalysts certain (poly)-halogenated phenoxathiins as cocatalysts. The cocatalysts are said to be of the following formula

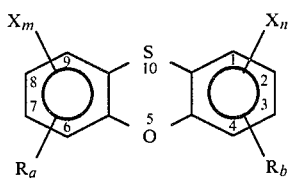

in which
R=H or $C_1$–$C_4$-alkyl,
a=0 to 4−m,
b=0 to 4−n,
x=Cl, Br, F,
m+n=2 to 8.

According to the cited Japanese Offenlegungsschrift, the cocatalysts are prepared by reacting unsubstituted or methyl-substituted diphenyl ether with sulfur or a sulfur chloride in the presence of $AlCl_3$ as a catalyst in accordance with the method in Organic Syntheses Coll. Vol. 2 pages 485/86, with subsequent halogenation. According to the examples of said Japanese Offenlegungsschrift, the halogenation is effected with chlorine or bromine in the presence of an $SbCl_5$ catalyst at temperatures between 70° and 180° C. in $CCl_4$ as solvent. For the preparation of, for example, tetrachlorinated 3-methylphenoxathiin it is possible to indicate the following reaction diagram:

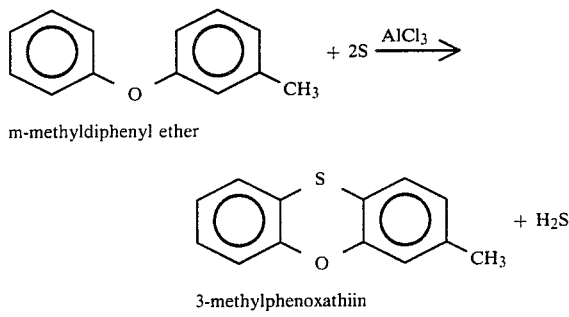

m-methyldiphenyl ether 3-methylphenoxathiin

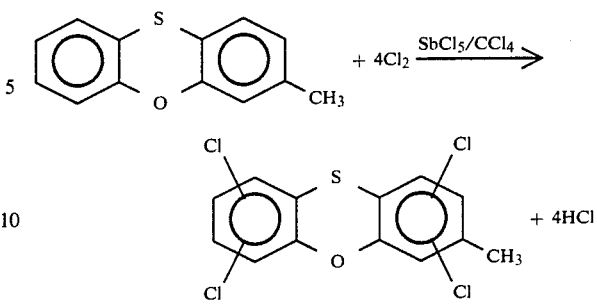

The chlorine substituents in the end compound can however also be differently distributed, that is, it is also possible for one of the two terminal aromatic rings to be trisubstituted or tetrasubstituted by chlorine and for the other to be substituted only once or not at all by chlorine.

The most favorable illustrative embodiment in said Japanese Offenlegungsschrift, i.e. the example in which the highest ratio of p-chlorotoluene:o-chlorotoluene and also the highest ratio of p-chlorotoluene:monochlorotoluene (o+m+p) is obtained, is Example No. 6. The p-/o- ratio there is 50.3/37.9=1.33, and the ratio p-/monochlorotoluene=57%. The example uses $SbCl_3$ as the catalyst and chlorinated 3-methylphenoxathiin having a chlorine content of 4.8 as cocatalyst, at 20° C.

Said Japanese Offenlegungsschrift names as preferred halogenated phenoxathiins, inter alia, also chlorinated dimethylphenoxathiins, including dimethyltetrachlorophenoxathiin. However, nothing is said about the positions of the methyl groups and the chlorine atoms; nor are there any illustrative embodiments present using chlorinated dimethylphenoxathiins. Because of the practically infinitely large number of conceivable isomeric chlorinated dimethylphenoxathiins, the mention of said compound in the cited Japanese Offenlegungsschrift without specifying the particular isomer is not very meaningful.

The phenoxathiin cocatalysts described in the above-mentioned Japanese Offenlegungsschrift have been further developed by the firm of Hodogaya Kagaku Kogyo K.K. for the purpose of further increasing the proportion of p-isomer in the ring chlorination of toluene in the presence of Lewis acid catalysts. In European Offenlegungsschrift No. 0,063,384 of this firm, the cocatalysts used are other specific chlorinated phenoxathiins. Before the chlorination these phenoxathiins have the following formula:

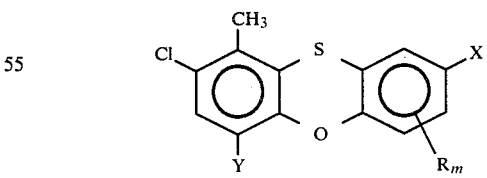

in which
R=$CH_3$ in the 1- and/or 3-position,
m=0, 1 or 2
X=H or Cl,
Y=Cl or $CH_3$,
where
m=1 or 2 and X=H or Cl for Y=Cl,
X=Cl for Y=$CH_3$ and m=0, and X=H for Y=CH₃ and m=1 or 2.

According to page 7 of said European Offenlegungsschrift, it is essential for cocatalyst effectiveness that before the chlorination (A) 9-methyl-6,8-dichlorophenoxathiin has a methyl group or groups in the 1- and/or 3-position and a hydrogen or chlorine atom in the 2-position or (B) that 6,9-dimethyl-8-chlorophenoxathiin is substituted in the 1- and/or 3-position by methyl or in the 2-position by chlorine if there is no methyl group in the 1- and/or 3-position.

The phenoxathiins mentioned in this European Offenlegungsschrift are in principle prepared in the same way as the cocatalysts described in the abovementioned Japanese Offenlegungsschrift. In the European Offenlegungsschrift, however, it is additionally stated how the corresponding starting diphenyl ethers are obtained (by Ullmann reaction of bromoaromatics with phenol (derivatives) in the presence of a copper catalyst), for example

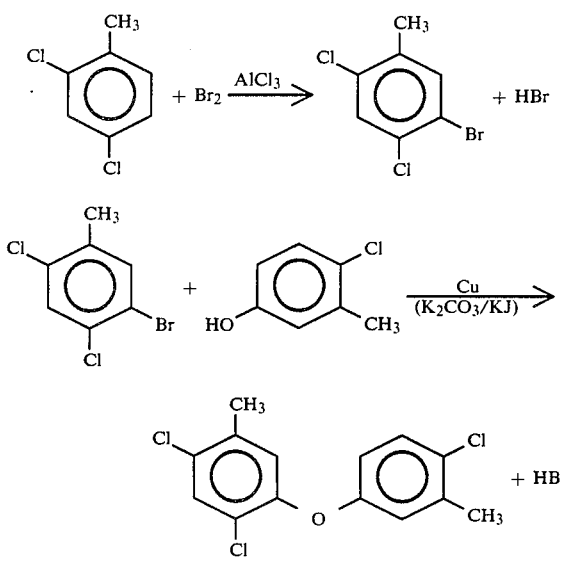

With regard to obtaining the highest proportion of p-chlorotoluene, the most favorable examples of the European Offenlegungsschrift are Examples 15 and 16.

In Example 15 the p-/o- ratio is 59.1/39.1 = 1.51 and the p-/monochlorotoluene share is 60.4%. The example uses SbCl₅ as the catalyst and chlorinated 3,6,9-trimethyl-8-chlorophenoxathiin of an average chlorine content of 3.1 as cocatalyst, at 20° C. (chlorination degree 0.99).

In Example 16 the p-/o- ratio is 56.8/36.8 = 1.54 and the p-/monochlorotoluene share is 60.7%. This example uses SbCl₃ as the catalyst and chlorinated 3,6,9-trimethyl-8-chlorophenoxathiin of an average chlorine content of 2.0 as cocatalyst, likewise at 20° C. (chlorination degree 0.94).

Although the p-/o- and p-/monochlorotoluene ratios obtained there are not unfavorable, it was desirable because of the fairly considerable proportion of in particular the o-isomer which is also formed and is the object of the present invention to improve the ring chlorination of toluene further in favor of the formation of p-monochlorotoluene, in particular since the abovementioned European Offenlegungsschrift also says (cf. page 2 paragraph 2) that an increase in the p-/monochlorotoluene share by as little as 0.5% is of high economic value.

This object is achieved according to the invention by using chlorinated 2,8-dimethylphenoxathiin.

The invention accordingly provides a process for ring-chlorinating toluene in the presence of Lewis acids as catalysts and of chlorinated dimethylphenoxathiin as cocatalyst, which comprises using as the chlorinated dimethylphenoxathiin the product which is obtained by chlorinating 2,8-dimethylphenoxathiin with about 4 mol of Cl₂/mol of 2,8-dimethylphenoxathiin in the presence of a Lewis acid—preferably SbCl₃ and/or SbCl₅—as catalyst at temperatures between about 70° and 120° C., if desired in an inert solvent, and which mainly comprises 1,3,7,9-tetrachloro-2,8-dimethylphenoxathiin of the formula

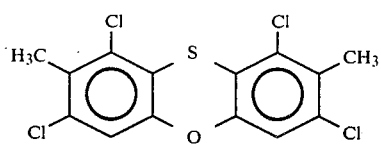

The process produces a p-/o- ratio of usually above 1.6 and a p-/monochlorotoluene share of usually above 62%—which represents an appreciable advance in view of the abovementioned statement on page 2 paragraph 1 of said European Offenlegungsschrift No. 0,063,384.

The technique provided by the invention for further shifting the isomeric ratio in the ring chlorination of toluene in favor of the p-isomer is very surprising since, owing to the large number of very similar phenoxathiin derivatives described as cocatalysts in Japanese Offenlegungsschrift No. 56-110,630 and European Offenlegungsschrift No. 0,063,384, it was unlikely that another, and a relatively little-modified phenoxathiin derivative would give a further improvement and since the phenoxathiin derivative used according to the invention does not meet the criteria which are specified in said European Offenlegungsschrift No. 0,063,384 (page 7) for the corresponding cocatalytic effectiveness.

The cocatalyst used according to the invention is prepared in principle as specified in Japanese Offenlegungsschrift No. 56-110,630 and European Offenlegungsschrift No. 0,063,384 for the phenoxathiin derivatives described there. In the present case, the starting compound is di-p-tolyl ether which in turn is obtainable, for example, by Ullmann reaction of p-chlorotoluene and p-cresol.

Di-p-tolyl ether is then heated with sulfur in the presence of AlCl₃ to form 2,8-dimethylphenoxathiin:

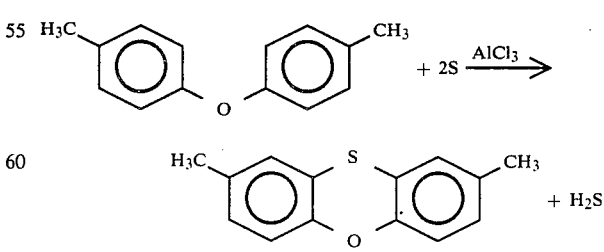

2,8-Dimethylphenoxathiin is chlorinated with about 4 mol of chlorine/mol of 2,8-dimethylphenoxathiin in the presence of a Lewis acid as catalyst. The Lewis acid catalyst used can in principle be any known Lewis acid, such as, for example, the oxides and halides of aluminum, tin, titanium, antimony, iron etc.; SbCl$_3$ and/or SbCl$_5$ are preferred.

The catalyst concentration is generally between about 0.001 and 5% by weight, preferably between about 0.1 and 2% by weight, relative to 2,8-dimethylphenoxathiin.

The reaction temperature for the chlorination is between about 70° and 120° C.

The chlorination can be carried out in the absence or presence of inert solvents; however, it is preferable for such solvents to be present since the reaction mixture is easier to handle as a result. Inert solvents which can be used are preferably lower aliphatic chlorohydrocarbons, such as, for example, carbon tetrachloride or tetrachloroethylene.

The solutions prepared by means of the solvent are advantageously about 5 to 20% by weight strength in 2,8-dimethylphenoxathiin.

In the chlorination of 2,8-dimethylphenoxathiin in the manner described above, the product is mainly—i.e. to at least about 50% - 1,3,7,9-tetrachloro-2,8-dimethylphenoxathiin. The byproducts formed are minor amounts of in particular trichlorinated and pentachlorinated 2,8-dimethylphenoxathiin. The structure of the compounds was established by means of NMR spectroscopy.

The sulfur content of the chlorination product is normally between about 8 and 9%, and the chlorine content between about 37 and 39%. The theoretical values for tetrachlorodimethylphenoxathiin are 8.74% (S) and 38.7% (Cl). The process of the invention for ring-chlorinating toluene is otherwise carried out in practically the same way as is described for the corresponding processes in Japanese Offenlegungsschrift No. 56-110,630 and European Offenlegungsschrift No. 63,384—except for the significant difference that in the present case a different cocatalyst is used.

The chlorination degree is at most = 1. Higher values would lead increasingly to undesirable polychlorination.

The Lewis acid catalysts used can be virtually any possibe Lewis acids; some Lewis acids which may serve as examples have been listed above in the description of the chlorination of 2,8-dimethylphenoxathiin.

The amount of catalyst and of cocatalyst is normally between about 0.005 and 5% by weight, preferably between about 0.05 and 0.5% by weight, relative to the starting toluene.

The chlorination of toluene is advantageously carried out within the temperature range between about 0° and 80° C., in particular between about 0° and 40° C. The preferred reaction pressure is atmospheric pressure, although in certain circumstances it is also possible to use subatmospheric or superatmospheric pressure.

To dilute the reaction mixture it is possible if desired to add an inert solvent; however, that yields no particular benefit.

The process can be carried out continuously and discontinuously.

The reaction mixture is worked up in conventional manner, preferably by distillation. Owing to the low o- and m-chlorotoluene contents, the preparation of p-chlorotoluene in the pure form by distillation no longer requires extremely high separating efficiencies.

From an industrial standpoint it is also important that the cocatalyst itself can be recovered from the crude chlorination mixture after the liquid constituents have been distilled off and be reused without loss of effectiveness.

The following examples are intended to illustrate the invention in more detail. The Examples relating to the invention are preceded by the preparative method for the cocatalyst.

PREPARATION OF THE COCATALYST (a) 2,8-Dimethylphenoxathiin 120 g (=0.6 mol) of di-p-tolyl ether were melted in a stirred flask, and 45 g (=0.34 mol) of AlCl$_3$ were added; this was followed at 70° to 80° C. by 20 g (=0.625 mol) of sulfur. The temperature was raised to 100° C. and maintained there for some hours. The mixture was then decomposed by pouring into dilute hydrochloric acid; a heavy oil deposit formed and was separated off. The oil was dried and fractionated in vacuo to isolate the 2,8-dimethylphenoxathiin.

The fractionation of the crude oil, which amounted to about 127 g, returned 48% of the starting di-p-tolyl ether as first cut. After a small intermediate cut the 2,8-dimethylphenoxathiin distilled over with a boiling point of >68° C.

Yield: 60.5 g (=44% of theory, =84% relative to reacted di-p-tolyl ether).

The sulfur content was 14.3% (theory 14.0%).

(b) Chlorinated 2,8-dimethylphenoxathiin 114 g (=0.5 mol) of 2,8-dimethylphenoxathiin were dissolved in 600 ml=1,000 g (=6 mol) of tetrachloroethylene, and 2 g of SbCl$_3$ were added.

The solution was heated to 100° C. 140 g (=2 mol) of chlorine gas were then passed in in the course of 5 to 6 hours. The temperature was then reduced to about 60° C., 800 ml of methanol were added, and the chlorinated product crystallized out. The crystals were filtered off with methanol at 30° C., were sucked dry and were dried in vacuo. Melting point 145°-150° C.

Yield: 150 g=82% of theory.

Sulfur content: 9.0% (theory 8.74% of S for tetrachloro compound).

Chlorine content: 37.5% (theory 38.7% of Cl for tetrachloro compound).

INVENTION EXAMPLES

EXAMPLE 1

2 g of SbCl$_3$ and 4 g of the cocatalyst prepared as described above were added to 1,400 g (=15.2 mol) of toluene. A slow stream of chlorine was passed in with cooling at 20° C. until a density of 1.043 was recorded. The deep bluish green solution was washed until neutral. The crude mixture still contained 16% of toluene. The monochlorotoluene fraction had the following composition:

37% of o-,
0.4% of m- and
61.6% of p-chlorotoluene.

The residue left behind amounted to about 3 to 4 g.

The p-/o- ratio was thus 1.66, and the p-/monochlorotoluene share was 62.2%.

EXAMPLE 2

Example 1 was repeated, except that chlorination was carried out until the mixture had a density of 1.064. Working up was effected as in Example 1. The crude mixture still contained 6.9% of toluene.

The monochlorotoluene fraction was composed of
36% of o-, 0.3% of m- and
60% of p-chlorotoluene.

The residue amounted to 3 g (in the main catalyst).

The p-/o- ratio was thus 1.67 and the p-/monochlorotoluene share was 62.3%.

EXAMPLE 3

Example 1 was again repeated, except that the Lewis acid catalyst used was not SbCl₃ but 1 g of FeCl₃ and the chlorination was carried out at 5° C. The chlorination was carried out as in Example 1 up to a density of the mixture of 1.043. After the deeply bluish green solution had been washed until neutral, the crude mixture still contained 15% of toluene.

The monochlorotoluene fraction was composed of
1.1% of toluene,
40% of o-,
0.3% of m- and
59% of p-chlorotoluene.

The p-/o- ratio was in this instance 1.475 and the p-/monochlorotoluene share was 60%.

EXAMPLE 4

Toluene was chlorinated with the cocatalyst recovered from Example 1.

The cocatalyst was recovered from Example 1 by taking up the almost dry residue, which was obtained in the fractionation of the chlorination mixture in Example 1, with methanol, filtration and drying. This gave about 3 g having a melting point of 148°–159° C.

For the chlorination, 2 g of the recovered cocatalyst were dissolved in 700 g (=7.6 mol) of toluene, 1 g of SbCl₃ was added, and the mixture was reacted at 20° C. with chlorine gas up to a density of 1.045.

The monochlorotoluene fraction contained 59% of p-chlorotoluene. The flask content was distilled off to dryness. The undiminished effectiveness of the recovered cocatalyst is hence conspicuous.

I claim:

1. A process for ring-chlorinating toluene, which comprises contacting toluene and chlorine in the presence of a first Lewis acid as a first catalyst and of chlorinated dimethylphenoxathiin as cocatalyst, wherein the chlorinated dimethylphenoxathiin is obtained by chlorination of 2,8-dimethylphenoxathiin with about 4 mol of chlorine/mol of 2,8-dimethylphenoxathiin in the presence of a second Lewis acid as a second catalyst at temperatures between about 70° and 120° C. to form mainly 1,3,7,9-tetrachloro-2,8-dimethylphenoxathiin of the formula

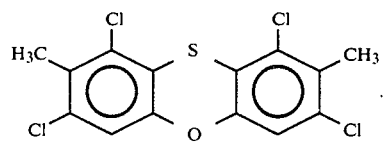

2. The process as claimed in claim 1, wherein the chlorinated 2,8-dimethylphenoxathiin has a sulfur content of about 8 to 9% and a chlorine content of about 37 to 39%.

3. The process as claimed in claim 1, wherein the ring chlorination of toluene leads to a chlorination degree of at most 1.

4. The process as claimed in claim 1, wherein the first catalyst and the cocatalyst are each used in an amount of about 0.005 to 5% by weight relative to the starting toluene.

5. The process as claimed in claim 1, wherein the ring chlorination is carried out at a temperature between about 0° and 80° C.

6. The process as claimed in claim 1, wherein the second Lewis acid is selected from the group consisting of SbCl₃ and SbCl₅.

7. The process as claimed in claim 1, wherein the chlorination of 2,8-dimethylphenoxathiin is carried out in an inert solvent.

8. The process as claimed in claim 1, wherein the first catalyst and the cocatalyst are each used in an amount of about 0.05 to 0.5% by weight.

9. The process as claimed in claim 1, wherein the ring chlorination is carried out at a temperature between about 0° and 40° C.

* * * * *